United States Patent [19]

Nyqvist et al.

[11] Patent Number: 5,626,869

[45] Date of Patent: *May 6, 1997

[54] PHARMACEUTICAL COMPOSITION CONTAINING A DEFINED LIPID SYSTEM

[75] Inventors: Håkan Nyqvist, Tullinge; Monica Einarsson, Upsala; Christer Mattsson, Kungsbacka, all of Sweden

[73] Assignee: Pharmacia & Upjohn AB, Stockholm, Sweden

[ * ] Notice: The term of this patent shall not extend beyond the expiration date of Pat. No. 5,469,840.

[21] Appl. No.: 497,381

[22] Filed: Jun. 29, 1995

Related U.S. Application Data

[63] Continuation of Ser. No. 321,620, Oct. 12, 1994, abandoned, which is a continuation of Ser. No. 142,345, Nov. 23, 1993, abandoned.

[30] Foreign Application Priority Data

Mar. 27, 1992 [SE] Sweden ............................... 9200951
Mar. 26, 1993 [WO] WIPO ..................... PCT/SE93/00258

[51] Int. Cl.$^6$ ................... A61K 9/127; A61K 9/16
[52] U.S. Cl. .................. 424/450; 424/489; 264/41; 428/402.2
[58] Field of Search ............................... 424/450, 489; 428/402.2; 264/4.1, 4.3; 514/56

[56] References Cited

U.S. PATENT DOCUMENTS

| | | | |
|---|---|---|---|
| 4,610,868 | 9/1986 | Fountain et al. | 424/1.1 |
| 4,877,561 | 10/1989 | Iga | 264/4.3 |
| 4,963,367 | 10/1990 | Ecanow | 424/485 |

FOREIGN PATENT DOCUMENTS

| | | |
|---|---|---|
| 10736/88 | 7/1988 | Australia . |
| 0084169A1 | 7/1983 | European Pat. Off. . |
| 0260241A1 | 3/1988 | European Pat. Off. . |
| 3331009 | 3/1985 | Germany . |
| 0007934 | 1/1985 | Japan . |
| WO84/02076 | 6/1984 | WIPO . |
| WO86/05694 | 10/1986 | WIPO . |

OTHER PUBLICATIONS

Bates et al., Bioavailability of Micronized Griseofulvin from Corn-Oil-in-Water Emulsion, Aqueous Suspension, and Commercial Tablet Dosage Forms in Humans, Journal of Pharmaceutical Sciences, vol. 64, No. 5, 1975, pp. 793–797.

Palin et al., The oral absorption of cefoxitin from oil and emulsion vehicles in rats, International Journal of Pharmaceutics, vol. 33, 1986, pp. 99–104.

Patel et al., Oral Administration of Insulin by Encapsulation within Liposomes, FEBS Letters, vol. 62, No. 1, 1976, pp. 60–63.

Flynn, Oral Delivery of Insulin, The Lancet, 1989, pp. 1518–1519.

Tarr et al., Enhanced Intestinal Absorption of Cyclosporine in Rats Through the Reduction of Emulsion Droplet Size, Pharmaceutical Research, vol. 6, No. 1, 1989, pp. 40–43.

Illum et al., Enhanced nasal absorption of Insulin in rats using lysophosphatidylcholine, International Journal of Pharm., vol. 57, 1989, pp. 49–54.

Woolfrey et al., The Effect of Miglyol 812 Oil on the Oral Absorption of Propranolol in the Rat, J. Pharm. Pharmacology, vol. 41, 1989, pp. 579–581.

Winn et al., The Bioavailability of a Mixed Micellar Preparation of Vitamin $K_1$, and its Procoagulant Effect in Anticoagulated Rabbits, J. Pharm. Pharmacology, vol. 41, 1989, pp. 257–260.

Rowland et al., The Stability of Liposomes in Vitro to pH, Bile Salts and Pancreatic Lipase, Biochimica et Biophysica Acta, vol. 620, 1980, pp. 400–409.

Manosroi et al., Thermodynamic Characteristics of a Human Insulin–Deae–Dextran Complex Entrapped in Liposomes, Drug Development and Industrial Pharmacy, vol. 16, No. 5, 1990, pp. 837–854.

Weiner et al., Liposomes as a Drug Delivery System, Drug Development and Industrial Pharmacy, vol. 15, No. 10, 1989, pp. 1523–1554.

Payne et al., Characterization of Proliposomes, Journal of Pharm. Sciences, vol. 75, No. 4, 1986, pp. 330–333.

*Primary Examiner*—Gollamudi S. Kishore
*Attorney, Agent, or Firm*—Pollock, Vande Sande & Priddy

[57] ABSTRACT

The present invention relates to pharmaceutical compostions containing a defined lipid system of at least two lipid components where at least one of the lipid components is amphiphatic and polar and one is nonpolar wherein the pharmaceutically active compound is a heparin or a fragment thereof. In the compositions a water containing solvent also is included in such an amount that discrete lipid particles are present, and said compositions can be adapted to various administration forms such as rectal, oral, buccal, transdermal etc.

15 Claims, No Drawings

PHARMACEUTICAL COMPOSITION CONTAINING A DEFINED LIPID SYSTEM

This application is a continuation application of U.S. patent application Ser. No. 08/321,620, filed Oct. 12, 1994, now abandoned which in turn, is a continuation of Ser. No. 08/142,345 filed Nov. 23, 1993 now abandoned.

FIELD OF INVENTION

The present invention relates to pharmaceutical compositions that contain a defined lipid system of at least two lipid components where at least one of the lipid components is amphiphatic and polar and one is non polar, wherein the pharmaceutically active compound is a heparin, a fragment or derivatives thereof. The compositions further contain an aqueous solvent in an amount such that discrete lipid particles are present and said compositions can be adapted to various administration forms such as rectal, oral, buccal, sublingual, transdermal etc.

DESCRIPTION OF THE INVENTION

This invention is based on a defined lipid system, described in the Swedish patent application SE 9003100-6, of at least two lipid components chosen from classes of different polarity, in which at least one of the compounds is amphiphatic and polar and one is non polar.

The amphiphatic and polar compound is bilayer forming and discrete lipid particles are formed spontaneously from the lipid system when it interacts with an excess amount of water or water containing solvents.

A defined lipid component is a lipid whose chemical composition is known and controlled. This will be explained more in detail below and in the Examples.

The property "bilayer forming" is a well-known physical parameter and can be established readily by suitable physicochemical methods (e.g. surface balance method). And the formed discrete lipid particles can be established by physical and/or chemical methods, such as microscopy using polarized light, image analysis or diffraction methods.

The variation in the lipid composition provides the control mechanism by means of which lipid particles are formed and thereby the rate of the lipid particle formation which will serve as a controlling factor for either immediate or sustained release of the entrapped or associated bioactive materials.

The following definitions are used:

lipids—a general term for natural or synthetic compounds consisting of acyl carriers, such as glycerol, sphingosine, cholesterol, and others or derivatives thereof, to which one or more fatty acids are or can be linked. Also similar molecules that contains a substantial hydrocarbon portion may be included.

The lipids used for the lipid particle forming systems can be grouped into different lipid classes, dependent on their polarity, namely:

non polar lipid classes—have no polar head groups or a hydrophilic part which is so small or so sterically hindered that it cannot interact with water. Examples of non polar constituents are hydrocarbons, or non-swelling amphiphiles, such as mono-, di- and triacylglycerols, cholesterol, fatty alcohols or cholesterol esters.

polar lipid classes—such as phospholipids or glycolipids, which have surface solubility due to a significant polar constituent. Depending on their specific interactions with water, they are further subdivided into the categories of swelling and soluble amphiphiles respectively.

amphiphatic or amphiphilic lipid classes—such as phospholipids and glycolipids, having surface activity, bilayer forming lipid classes—amphiphatic lipids, such as PC (phosphatidylcholine), sphingomyelin, PI (phosphatidylinositol) or PE (phosphaditylethanolamine) with a molecular geometry that preferentially forms bilayer structures in the presence of water.

The lipids used for the carrier systems according to the present invention consist of a mixture of lipid classes characterized by their different polarities. Polar lipids, such as phospholipids or glycolipids, and non polar lipids, such as mono-, di- and triglycerides, are the main constituents in the system although sterols, such as cholesterol, fatty acids, fatty alcohols and esters thereof as well as other lipid classes may be also be used. This well defined mixture of lipids from different classes as defined above, should not be confused with commercial products such as soybean oil, maize oil or soy lecithin and egg lecithin. To obtain the well defined lipid classes the commercial oil is fractionated and then the different lipids classes are admixed as is explained in more detail in the Examples below. Another way to obtain well defined lipid classes is to use synthetically produced lipids.

Furthermore, derivatives of lipids may also be used in combination with the above mentioned lipids. One examples of this is polyethylene glycol coupled to phosphatidylethanolamine, which has shown to prolong the circulation time of liposomes after injection in the blood stream. Another example of such a derivative is palmitoylcarnitine, which acts as an absorption enhancer for bioactive substances in the gut.

In a suitable way of initiating the formation of the lipid carrier system, the bioactive substance is admixed to a selected lipid, followed by admixing of a lipid of a different polarity. This polar/non-polar alteration may be continued for as many cycles as necessary in the specific case, involving a range of lipids with different polarities.

The preferred way of incorporation of a bioactive substance into the lipid carrier system is to admix the bioactive substance to amphiphilic lipids in order to create a homogenous formulation, where the amount of amphiphilic lipids generally are in the total range of 1–90% w/w. Such an amphiphilic lipid shall be capable of spontaneous bilayer formation. Examples thereof are amphiphilic and polar lipid classes, such as phosphatidylcholine, phosphatidylglycerol, phosphatidylinositol or phosphatidylserine or mixtures thereof.

The design of the lipid carrier system includes not only the proper selection and/or combination of lipid classes, tailor-made for the solubilization of each bioactive substance, but also the proper selection of the distribution of fatty adds, i.e. the acyl groups attached to the lipid classes used. Variation of the acyl groups gives different physiochemical properties as will be seen in the examples below.

The rate by which lipid particles are formed from the system in a given aqueous environment can be influenced and controlled by varying the geometrical shape of the main bilayer forming lipid class, i.e. the effective head group area in relation to the steric conformation of the hydrocarbon tails.

A second way of influencing and controlling the formation of lipid particles is by varying the structure, thus the fluidity, of the hydrocarbon chains in the non polar part of the lipid system. This will influence the rate of interaction of the endogenous amphiphatic lipids and the exogenous aqueous medium.

DETAILED DESCRIPTION OF THE INVENTION

According to the present invention the aforedescribed defined lipid system is utilized in a pharmaceutical composition that contains a heparin, a fragment or derivatives thereof with a water containing solvent. The expression "a heparin" denotes any fraction or class of heparin from natural, biosynthetical, synthetical or genetically engineered sources, as well as any derivative i.e. heparin esters and "fragment thereof" denotes any low molecular weight fragment of heparin or their derivatives including chemically modified synthetic heparin-like oligosaccharides.

In many non-parenteral administration forms considerable difficulties have been experienced in overcoming the poor bioabsorption of heparins.

An object of this invention is to solve this problem by providing a flexible composition based on the mentioned lipid system.

Another object of the invention is to provide a composition well-suitable for convenient forms of long-term self administration of heparins as alternatives to parenteral administration.

Such a composition can be used for the manufacture of preparations adapted for an oral, rectal, buccal, sublingual, nasal, subcutaneous or any transmembrane or transdermal administration, by adding suitable vehicles, solvents or carriers for each appropriate administration route.

The amphiphatic and polar compound is preferably phosphatidylcholine and the non polar lipid is preferably chosen from mono-, di- or triglycerides.

The amount of water in the composition should be of such significance that discrete lipid particles are formed.

This condition has to be tested for each lipid system, because the actual limit for the system to form lipid particles is dependent on the nature and the composition of the lipid components and the nature of the bioactive component to be administered by the system.

The most important considerations when choosing the components of the lipid system are the constitution of the lipids and the polarity of the bioactive drug to be incorporated in the system.

The absorption can be controlled, by varying the chain length of the glycerides between six to eighteen carbon atoms, preferably between six to twelve carbon atoms. The choice of polarity and the choice of differently charged groups of the constituents can also influence the lipid particle formation.

The lipid particles may be a mixed population containing different mono- bi- and multilayered structures such as micelies, liposomes, and higher multilayered structures.

There are a number of methods well known in the art for controlling the population both in size range and in structure such as sonication, freeze-thawing controlled stirring and various size range influencing equipments. The need of such devices is to be considered separately for each administration form and each therapeutically active compound to be delivered with the composition.

The composition of the lipid particle population is also influenced by the choice of lipid material in terms of polarity, carbon chain length(s) and other factors as discussed above.

In a preferred composition according to the invention the compound is a heparin or a fragment thereof and the lipid system comprises a phosphatidylcholine as an amphiphilic compound and a monoglyceride as the non polar component.

The amount of amphiphilic compounds in the composition may be within the range of 1-90% (w/w) of the lipid system, preferably between 1-50% (w/w) and most preferably between 5-50% (w/w) with respect to the lipid system.

A preferred heparin fragment is Fragmin®, which is a low molecular weight heparin fragment prepared by Kabi Pharmacia from porcine heparin by a controlled nitrous acid depolymerisation process, see EP 14184. Fragmin® may be in the form of a solution or a suspension, when added to or mixed with the other components of the composition. It may also be admixed with the essentially water free lipid matrix before the other constituents of the compositions are added.

Fragmin® is very readily soluble in water and such aqueous solutions are considered to be stable.

The properties of Fragmin® makes possible numerous preparations based upon the defined lipid system with the addition of suitable excipients.

Such preparations may be adapted for rectal use in the form of foams, clysmas, capsules and suppositories or different preparations specially manufactured for oral, buccal, sublingual, nasal, transdermal and subcutaneous administration or for administration through mucous membranes in general. The inventive composition containing Fragmin® and defined lipids is also suitable for the manufacture of a depot preparation for obtaining sustained release for e.g. subcutaneous administration or for application to a porous polymeric matrice with mucoadhesive properties for e.g. buccal administration.

The preparations are useful for treating and/or preventing a wide variety of pathological processes such as thromboembolic diseases, pre-infarctional angina, coronary heart diseases, inflammatory diseases, thrombophlebitis, autoimmune diseases, arteriosclerosis or for treatment of methasthasis or angiogenesis related diseases.

Any adaptation of the compositions for the above-mentioned administration routes for any mentioned treatment will be obvious to persons skilled in this art.

The total dosage of Fragmin® in the above-mentioned administration forms can thus be very high and is limited only by the bioavailability and by that which is therapeutically or clinically appropriate to administer and that which is well tolerated.

Examples of clinical doses are 120 IU per kg body weight twice daily for deep venous thrombosis and for thrombosis prophylaxis (for low risk patients) 2500 IU per day or 5000 IU per day (for high risk patients).

For example, the relative amount of Fragmin® to lipids may be in the range of 1-200 (w/w), preferably 2-80 (w/w).

However a higher amount of both Fragmin® and lipids are conceivable within the context of the invention if it is clinically suitable.

If the amount of lipids will be to low in a composition the enhanced absorption effect will be reduced, which may be compensated by an increased amount Fragmin® in order to obtain the same serum levels after administration.

This broad concentration range, which makes possible Fragmin® to lipid in a relative amount of up to 200 (w/w) indicates the flexibility of the components to be adapted to a composition for suitable dosage forms to be delivered to different types of patients.

The solubility and stability of Fragmin® facilitates the adaption of the composition to a suitable administration form and furthermore there is a strong evidence that it might have a stabilising influence on the lipid particle population of the composition, probably due to its high negative charge density.

The following examples, which shall not be considered to limiting the scope of the invention, show Fragmin® in compositions with lipids defined in the examples in the proportions of 25% phosphatidylcholine as the amphiphilic compound and 75% monoglyceride as the non polar compound.

The compositions have been administered rectally and intraduodenally in-vivo with various amounts of additional water based solvent. In the intraduodenally applied, compositions the water content may vary from 1 to 4 by parts of weight with respect to the lipid constituents of the composition.

The relative amounts of Fragmin® to lipid tested were from 2 up to 200 (w/w).

Examples 1–5 below illustrate the variation of the lipid constituents of the lipid system, in the absence of bioactive compounds, by selection of lipids and combinations thereof without limiting the scope of protection.

Examples 6–7 show the preparation of compositions which contain the defined lipid system consisting of a phosphatidylcholine, glycerol esters and Fragmin®. These compositions does not initially comprise a water based solvent in an amount such that lipid particle formation direct will occur directly and spontaneously.

Example 8 shows the animal model used in the experiments in the following examples and the bioavailability of Fragmin® after an intraduodenal or rectal administration in the absence of the lipid system.

Example 9 shows that the intraduodenal absorption of Fragmin® is significantly increased when included in the lipid system.

Example 10 shows that intraduodenal absorption is increased when external water is added before administration.

Example 11 shows that the intraduodenal absorption is also similarly enhanced when the water in example 10 is exchanged with physiological saline in the same amount.

Example 12 shows that rectal absorption of Fragmin® is significantly higher when incorporated in the lipid system as compared with Fragmin® dissolved in physiological saline, in the absence of the lipid system.

Example 13 shows that the addition of external water or physiological saline to the lipid system has a positive effect on rectal absorption.

Examples 14 and 15 show that Fragmin® need not necessarily be included in the lipid system before dissolution with water or saline, in order to be absorbed from the duodenum or the rectum.

Example 16 illustrates that the tested commercially available crude lipids give a lower rectal absorption than the defined lipids.

Example 17 is a comparison of the absorption of different Fragmin® to lipid ratios and shows that the rectal absorption is high over a broad lipid and Fragmin® concentration range.

Example 18 is a comparison of the heparin and Fragmin® absorption in preparations which contain the lipid system.

Example 19 shows hat after formation of the composition, the solution can be stored at varying time lengths before administration without a significant influence of the absorption properties.

Example 20–21 shows that the Fragmin® activity is retained and its absorption is still high after prolonged storage of the composition.

The results show that the defined lipid system enhances intraduodenal absorption and that the highest absorption of intraduodenally applied Fragmin® is achieved with the highest tested water content of the composition. The tested concentrations of the components showed favourable results. However it may be possible to optimize the conditions still further.

The reasons for the enhanced absorption may be that a higher contact surface area between the composition and the intestinal membranes is obtained, but also probably because that the lipid particle population has an advantageous structural composition at the degree of dilution concerned.

The lipid particles may also protect the drug from enzymatical degradation in the intestines, both if the lipid particles carries the drug or if they are otherwise present in the solution. A large amount of lipids present may block the Fragmin® degrading enzymes and in such a case the Fragmin® might be well protected outside the lipid particles. However, when the amount lipids are low, it may be advantageous to enclose the Fragmin® within the lipid particles.

Enzyme inhibitors are a conceivable additive to the inventive compositions.

It is also noted that absorption is high, irrespective of whether Fragmin® is initially present free in the solution or incorporated in the lipid particles. Excellent absorption results are also shown after rectal administration of Fragmin® compositions with the lipid system in a wide range of present water or saline. These results are comparable with subcutaneous injections, which is the most common administration route today.

It is also shown that the defined lipid system is advantageous compared to commercial lipids in terms of controlling and stabilising the compositions as well as reproducing the absorption.

It is also observed that the size of the particles formed can vary considerably, without influencing the favourable absorption properties of Fragmin®.

The compositions are shown to be equally useful after short and long periods of time after their preparation.

The compositions according to the invention also enable the heparin absorption to be enhanced, when administered with the lipid system. The defined lipid system used in the present invention is also advantageous because its well-defined constituents enable the biological absorption and also the release and solubilisation of the drug to be controlled more accurately.

This means the choice of appropriate lipid constituents from the lipid classes will enable a better control of the absorption to be achieved. It is also noted that high absorption can be obtained even if Fragmin® is not included in the lipid system during the manufacturing, but added as a solution to a lipid composition during shaking or sonication.

In conclusion it must be considered that compositions based on the defined lipid system and heparins or heparin fragments are surprisingly favourable in terms of enhanced absorption and provide an advantageous possibility of controlling the absorption rate.

Various modifications and equivalents will be apparent to one skilled in the art and may be used in the compounds, compositions and methods of the present invention without departing from the spirit or scope thereof, and it is therefore to be understood that the invention is not to be limited to the specific examples and embodiments herein.

EXAMPLES

Example 1

1.25 g phospholipids from soybean (I) were added to 1.25 g of a glyceride mixture (II) and gently stirred for 12 hours at 60° C. 2.50 g of a triglyceride (III) were then added and the total mixture was stirred for 1 hour at 60° C.

| Lipid class composition (g) | I | II | III | Fatty acid composition of triglyceride (wt %) | |
|---|---|---|---|---|---|
| Phosphatidylcholine | 0.50 | | | | |
| Phosphatidylethanolamine | 0.40 | | | | |
| Phosphatidylinositol | 0.23 | | | | |
| Non polar lipids | 0.12 | | | | |
| Monoacylglycerol | | 0.63 | | | |
| Diacylglycerol | | 0.63 | | | |
| Triacylglycerol | | | 2.50 | 8:0 caprylate | 58.5 |
| | | | | 10:0 caprate | 40.5 |
| | | | | 12:0 laurate | 0.6 |
| | | | | 16:0 palmitate | |
| | | | | 18:0 stearate | |
| | | | | 18:1 oleate | |
| | | | | 18:2 linoleate | |
| | | | | 18:3 linolenate | |
| | | | | minors | 0.4 |
| Total | 1.25 | 1.25 | 2.50 | Total | 100 |

Example 2

1.25 g phospholipids from soybean (I) were added to 1.25 g of a glyceride mixture (II) and gently stirred for 12 hours at 60° C. 2.50 g of a triglyceride (III) were then added and the total mixture was stirred for 1 hour at 60° C.

| Lipid class composition (g) | I | II | III | Fatty acid composition of triglyceride (wt %) | |
|---|---|---|---|---|---|
| Phosphatidylcholine | 0.40 | | | | |
| Phosphatidylethanolamine | 0.35 | | | | |
| Phosphatidylinositol | 0.18 | | | | |
| Phosphatic acid | 0.07 | | | | |
| Non polar lipids | 0.25 | | | | |
| Monoacylglycerol | | 0.63 | | | |
| Diacylglycerol | | 0.63 | | | |
| Triacylglycerol | | | 2.50 | 8:0 caprylate | 58.5 |
| | | | | 10:0 caprate | 40.5 |
| | | | | 12:0 laurate | 0.6 |
| | | | | 16:0 palmitate | |
| | | | | 18:0 stearate | |
| | | | | 18:1 oleate | |
| | | | | 18:2 linoleate | |
| | | | | 18:3 linolenate | |
| | | | | minors | 0.4 |
| Total | 1.25 | 1.25 | 2.50 | Total | 100 |

Example 3

1.25 g phospholipids from soybean (I) were added to 1.25 g of a glyceride mixture (II) and stirred gently for 12 hours at 60° C.

| Lipid class composition (g) | I | II |
|---|---|---|
| Phosphatidylcholine | 0.40 | |
| Phosphatidylethanolamine | 0.35 | |
| Phosphatidylinositol | 0.18 | |
| Neutral lipids | 0.07 | |
| Monoacylglycerol | | 0.63 |
| Diacylglycerol | | 0.63 |
| Triacylglycerol | | |
| Total | 1.25 | 1.25 |

Example 4

1.25 g phospholipids from soybean (I) were added to 1.25 g of a glyceride mixture (II) and 0.16 g ethanol. The total mixture was stirred gently for 6 hours at 60° C. 0.16 g of a triglyceride (III) was added and the total mixture is stirred for another hour at the elevated temperature.

| Lipid class composition (g) | I | II | III |
|---|---|---|---|
| Phosphatidylcholine | 0.40 | | |
| Phosphatidylethanolamine | 0.35 | | |
| Phosphatidylinositol | 0.18 | | |
| Neutral lipids | 0.32 | | |
| Monoacylglycerol | | 0.63 | |
| Diacylglycerol | | 0.63 | |
| Triacylglycerol | | | 0.16 |
| Total | 1.25 | 1.25 | 0.16 |

Example 5

2.50 g phosphatidylcholine from soybean (I) and 7.50 g of a monoglyceride (II) were stirred gently for 6 hours at 60° C. 1.25 g water were added and the stirring continued for another hour at the elevated temperature.

| Lipid class composition (g) | I | II |
|---|---|---|
| Phosphatidylcholine | 2.5 | |
| Monoacylglycerol | | 7.50 |
| Total | 2.50 | 7.50 |

Example 6

2.50 g phosphatidylcholine from soybean (I) and 7.50 g of a monoglyceride (II) were stirred gently for 6 hours at 60° C. 1.25 g Fragmin® solution (120 mg/g water) was added and the stirring continued for another hour at the elevated temperature.

| Lipid class composition (g) | I | II |
|---|---|---|
| Phosphatidylcholine | 2.5 | |
| Monoacylglycerol | | 7.50 |
| Total | 2.50 | 7.50 |

Example 7

2.50 g phosphatidylcholine from soybean (I) and 7.50 g of a monoglyceride (II) were stirred gently at 60° C. for 6 hours. 0.625 g Fragmin® solution (120 mg/g water) was added and the stirring continued for another hour at the elevated temperature.

| Lipid class composition (g) | I | II | Fatty acid composition of monoacylglycerol (w %) | |
|---|---|---|---|---|
| Phosphatidylcholine | 2.50 | | | |
| Monoacylglycerol | | 7.50 | | |
| | | | 8:0 caprylate | 78.4 |
| | | | 10:0 caprate | 21.2 |
| | | | 12:0 laurate | 0.2 |
| | | | minors | 0.2 |
| Total | 2.50 | 7.50 | Total | 100 |

The size distribution of the lipid particles formed in water at 37° C. was determined for Example 15, using a Malvern equipment. The formulation was shaken gently in water for 17 hours and then centrifuged as to separate the lipid phase from the aqueous phase. The following result was obtained.

| Size | % |
|---|---|
| <1 μm | 36 |
| >1 μm, <2 μm | 60 |

Example 8

Animal Model

New Zealand white rabbits of both sexes, weighing 2.5–3.5 kg were used in all experiments. After fasting for 12 hours, each animal was sedated with an intravenous injection of Hypnorm 0.1 ml/kg (Janssen Pharmaceuticals, Belgium) and a subcutaneous injection of Atropine, 0.5 mg/kg (Kabi Pharmacia, Sweden). The rabbits were anaesthetized with Mebumal, 20 mg/kg. The anaesthesia was subsequently maintained as required. The animals were shaved and a medial laparotomy performed. The test compounds were then injected directly into the duodenum, after which the peritoneal cavity was closed. Rectal administration was performed by means of a syringe coupled to a plastic tube designed for use in the rectum of rabbits. The dosage was checked by weighing of the syringe and connecting tubings before and after administering the test compounds.

Blood samples (1 ml) were collected at 0.25, 0.5, 0.75, 1, 1.5, 2, 2.5, 3, 4, 5, 6, 7, 8, 9, and 10 hours with the aid of catheter inserted in the ear artery and mixed with sodium titrate to a final concentration of 0.04M. The tubes were kept on ice until centrifuged at 800 g for 10 minutes. The anti-FXa activity in plasma was determined with an initial rate assay using bovine FXa (Kabi Pharmacia) and the chromogenic substrate S-2222.

The apparent bioavailability of Fragmin® after an intraduodenal or a rectal administration is expressed as a fraction of the area under the anti-FXa activity curve i.e. (AUC intraduodenal/rectal) and (AUC$_{s.c.}$) the latter determined to be 5.14±0.34 arbitrary units in 6 rabbits receiving a subcutaneous injection of Fragmin® at a dosage of 2 mg/kg.

Bioavailability of Fragmin® in the Absence of Lipids

The bioavailability of Fragmin® after an intraduodenal administration in the absence of the lipid system was tested in 4 rabbits. Two of the rabbits received Fragmin®, 25 mg/kg, as a powder included in a gelatine capsule which was placed in the duodenum at the pylorus level. The remaining two rabbits received Fragmin® dissolved in physiological saline, which was injected directly into the duodenum (total dosage 25 mg/kg). No anti-FXa activity could be detected in any of these animals over an observation period of 8–10 hours. The bioavailability of Fragmin® after a rectal administration was tested in 3 rabbits. Fragmin® was dissolved in physiological saline and injected directly into the rectum at a dosage of 10 mg/kg. Two of these rabbits had no detectable anti-FXa activity in plasma but one showed an activity of 0.2 IU/ml for 45 minutes which corresponds to a bioavailability of less than 1%.

Conclusion. The bioavailability of Fragmin® in the absence of enhancing additives is less than 1% after an intraduodenal or a rectal administration.

Example 9

The intraduodenal absorption of Fragmin® included in the lipid system according to Examples 5–7 was tested in 8 rabbits. The Fragmin®/lipid system was mixed with water in such an amount that discrete, individual lipid particles are formed, ten minutes before being applied into the duodenum. The composition of the mixture was as follows: 1 part (weight) Fragmin®/lipid+1 part (weight) distilled water. The water/lipid system was shaken vigorously for 5–10 minutes and then left to stand at room temperature for another 10 minutes before being injected into the duodenum. The concentration of Fragmin® was 2% of the lipid weight. All the rabbits received the following doses: Fragmin® 25 mg/kg, Lipids 1250 mg/kg and distilled water 1250 mg/kg. All rabbits in this experiment had detectable levels of anti-FXa activity in plasma. The maximal plasma concentration ($C_{max}$) was reached within 0.5–1.5 hours and ranged between 0.37 IU/ml to 1.76 IU/ml. The average absorption in this experiment was 4.7±3.0%.

Conclusion. The intraduodenal absorption of Fragmin® is significantly increased when included in the lipid system, as compared to the absence of lipids in the system.

Example 10

This experiment was identical to the study described in Example 9 with the exception that the Fragmin®/lipid system was mixed with a greater amount of water. The composition of the mixture was as follows: 1 part (weight) Fragmin®/lipid+4 parts (weight) distilled water. The concentration of Fragmin® was 2% of the lipid weight. All the rabbits (n=9) received the following doses: Fragmin® 25 mg/kg, Lipids 1250 mg/kg and distilled water 5000 mg/kg (≈5 ml). All rabbits in this experiment had detectable levels of anti-FXa activity in plasma. $C_{max}$ was reached within 0.75–1.5 hours and ranged between 0.73 IU/ml to 3.79 IU/ml. The average absorption in this experiment was 14.7±5.6%.

Conclusion: The intraduodenal absorption of Fragmin® is significantly increased when the lipid system (containing Fragmin®) is mixed with water before being injected into the duodenum.

Example 11

This experiment was identical to the study described in Example 10 with the exception that the Fragmin®/lipid system was mixed with 4 parts of physiological saline instead of the same amount of distilled water. This was done in order to study if the ionic strength of the Fragmin®/lipid/water system had any effect on the intraduodenal absorption of Fragmin®. The mixture had the following composition: 1 part (weight) Fragmin®/lipid +4 parts (weight) physiological saline. The concentration of Fragmin® was 2% of the lipid weight. All the rabbits (n=10) received the following dosage: Fragmin® 25 mg/kg, Lipids 1250 mg/kg and physiological saline 5000 mg/kg. All rabbits in this experiment had detectable levels of anti-FXa activity in plasma. $C_{max}$ was reached within 0.75–1.5 hours and ranged between 0.62 IU/ml to 2.60 IU/ml. The average absorption in this experiment was 13.4±7.3%.

Conclusion: The intraduodenal absorption of Fragmin® is significantly enhanced when the Fragmin®/lipid system is mixed with physiological saline.

Example 12

The rectal absorption of Fragmin® included in the lipid system was tested on 5 rabbits. The lipid system, without water, was injected directly into the rectum at a dose of 100 mg/kg corresponding to a Fragmin® dosage of 2 mg/kg. All rabbits in this experiment had detectable levels of anti-FXa activity in plasma. $C_{max}$ was reached within 1.5–2.5 hours and ranged between 0.53 IU/ml to 1.98 IU/ml. The average absorption in this experiment was 67.0±18.2%.

Conclusions. The rectal absorption of Fragmin® included in the lipid system without addition of an aqueous solution is dramatically higher than the rectal absorption of Fragmin® alone dissolved in physiological saline.

Example 13

Addition of external water or physiological saline to the lipid system had a positive effect on the intraduodenal absorption (See Examples 9, 10 and 11). This experiment was carried out in order to test if a similar effect could be seen after a rectal administration. Fragmin®/lipid system was mixed with 4 parts of physiological saline as described in Example 11 ten minutes before being administered to the rectum. The composition of the mixture was as follows: 1 part (weight) Fragmin®/lipid system+4 parts (weight) of physiological saline. The Fragmin® concentration was 2% of the lipid weight. This composition was tested in 7+7 rabbits at a Fragmin® dosage of 2 and 5 mg/kg, respectively. The lipid dosage was 100 and 250 mg/kg and the amount of physiological saline was 400 and 1000 mg/kg. The results are summarized in the table below.

| DOSE (mg/kg) | AUC (IU/ml × h) | Cmax (IU/ml) | ABSORPTION (%) |
| --- | --- | --- | --- |
| 2 | 4.4 | 1.43 ± 0.51 | 85.6 ± 29.7 |
| 5 | 11.8 | 2.89 ± 0.78 | 91.6 ± 30.0 |

Conclusion. The rectal absorption of Fragmin® included in the lipid system and mixed with external saline was almost as high as that observed after a subcutaneous injection, which today is the most commonly used route of administering Fragmin®. The rectal absorption of Fragmin® shows a good dose-proportionality as a 2.5-fold increase in the dosage results in a similar increase in AUC and Cmax while the absorption rate is constant.

Example 14

In all the experiments described above Fragmin® was included in the lipid system prior to the adding of water or physiological saline to the system. In the following experiments, exactly the same lipid system was used, but without included Fragmin®. This lipid composition, without Fragmin®, will in the following discussion be referred to as "placebo lipids".

The intraduodenal absorption of Fragmin® mixed with placebo lipids was tested on 7 rabbits. Fragmin® powder was dissolved in physiological saline to a final concentration of 5 mg/ml (0.5%). Four parts (weight) of this Fragmin® solution was mixed with 1 part (weight) of the placebo lipid. The concentration of Fragmin® in this mixture was 2% of the lipid weight, which is the same Fragmin®/lipid ratio as that in examples 11–15. The mixture was shaken vigorously for 5–10 minutes or alternatively sonicated for an appropriate length of time before being injected intraduodenally. All the rabbits received the following dosage: Fragmin® 25 mg/kg, Lipids 1250 mg/kg and distilled water 5000 mg/kg. All rabbits in this experiment had detectable levels of anti-FXa activity in plasma. The maximal plasma concentration ($C_{max}$) was reached within 0.5–2.0 hours and ranged between 0.53 IU/ml to 3.55 IU/ml. The average absorption in this experiment was 13±8%.

Conclusion: This experiment shows that Fragmin® need not necessarily be included in the lipid system prior to adding water, in order to be absorbed from the duodenum. A mixture of placebo lipids and water or saline, containing dissolved Fragmin®, is absorbed to a similar degree. Favourable results are obtained both by shaking and sonicating the composition.

Example 15

The rectal absorption of Fragmin® mixed with placebo lipids was tested in 6 rabbits. The mixture was prepared as described in Example 14 and injected rectally at the following dosage: Fragmin® 2 mg/kg, Lipids 100 mg/kg and physiological saline 400 mg/ml. All rabbits in this experiment had detectable levels of anti-FXa activity in plasma. $C_{max}$ was reached within 0.5–2.0 hours and ranged between 0.59 IU/ml to 1.95 IU/ml. The average absorption in this experiment was 64.2±31%.

Conclusion: This experiment shows in accordance with Example 14 that Fragmin® need not necessarily be included initially in the lipid system in order to be absorbed from rectum. A mixture of placebo lipids and saline, containing dissolved Fragmin®, is also absorbed to a higher degree than Fragmin® without lipids. (compare with Example 13).

Example 16

The rectal absorption of Fragmin® mixed with commercially available lipids was tested on 4 rabbits. The following commercial lipids were used: IMWITOR MG 742 (from MG Hüls AG, containing about 50% monoglycerides and 50% di- and triglycerides with acyl radicals principally derived from caprylic add and capric acid) and the phosphatidylcholine Zigma PC (P-5394 from Sigma, containing 84% PC, 13% PE and 3% other constituents). The commercial lipids were mixed with physiological saline as described in Examples 14 and 15 and injected rectally at the following dosage: Fragmin® 2 mg/kg, Lipids 100 mg/kg and physiological saline 400 mg/ml. Two out of 4 rabbits in this experiment had no detectable levels of anti-FXa activity in plasma and two had low levels in the range of 0.13 IU/ml to 0.25 IU/ml. The average absorption in this experiment was 0.7±1.5% (including those with no detectable absorption).

Conclusion: When the highly defined lipid system was exchanged for the cruder lipids from which they have been purified, a dramatic decrease in rectal absorption also was observed which demonstrates that the enhanced absorption described in a number of the Examples above is not an effect of lipids in general but can be ascribed to the effect of the defined lipid system.

Example 17

The amount of Fragmin® in relation to the amount of lipids has in the examples described above always been 2 mg/kg body weight per 100 mg/kg body weight. The following experiment was designed in order to study rectal absorption as a function of the Fragmin®/lipid ratio. One part of the placebo lipid system was mixed with 4 parts of physiological saline containing dissolved Fragmin® as described in Example 16, but with a 16 hour storage period. A higher Fragmin®/lipid ratio was obtained by increasing the amount of Fragmin® dissolved in saline. The following compositions were tested with respect to rectal absorption:

| group no | Fragmin ®/lipid mg/kg | mg Fragmin ®/100 mg lipid ratio | mg saline/kg |
|---|---|---|---|
| 1 (n = 8) | 2:100 | 2 | 400 |
| 2 (n = 9) | 2:50 | 4 | 200 |
| 3 (n = 8) | 2:25 | 8 | 100 |
| 4 (n = 7) | 2:10 | 20 | 40 |
| 5 (n = 8) | 2:5 | 40 | 40* |
| 6 (n = 8) | 2:2.5 | 80 | 40* |
| 7 (n = 4) | 2:1 | 200 | 15* |

*due to practical reasons (too small volumes) the lipid concentraions could not be kept constant. n is the number of rabbits tested.

The following results were obtained:

| Group no | Fragmin/lipid ratio | AUC | $C_{max}$ IU/ml | Absorption % |
|---|---|---|---|---|
| 1 | 2 | 3.0 ± 1.3 | 1.1 ± 0.4 | 53.2 ± 9.4 |
| 2 | 4 | 3.6 ± 1.1 | 1.1 ± 0.4 | 74.3 ± 17.3 |
| 3 | 8 | 4.6 ± 1.5 | 1.6 ± 0.5 | 86.0 ± 27.2 |
| 4 | 20 | 3.2 ± 1.4 | 1.3 ± 0.4 | 73.5 ± 18.1 |
| 5 | 40 | 3.7 ± 1.2 | 1.3 ± 0.6 | 80.1 ± 12.9 |
| 6 | 80 | 2.0 ± 1.1 | 0.6 ± 0.3 | 48.5 ± 20.9 |
| 7 | 200 | 1.0 ± 0.6 | 0.3 ± 0.2 | 20.7 ± 11.4 |

Conclusions: All the Fragmin®/lipid compositions tested gave a high rectal absorption which indicates that the concentration of Fragmin® and lipids in the described system give an increased absorption when compared to Fragmin® without lipids. The lipid composition has an enhancing effect on the rectal absorption of Fragmin®.

Example 18

Fragmin® is a low molecular weight heparin fragment prepared from porcine heparin by a controlled nitrous acid depolymerisation process. Several investigators have shown that heparin is poorly absorbed (<1%) after oral or intraduodenal absorption. The aim of the present study was to investigate if the lipid system could enhance the rectal absorption of heparin. The experimental procedure was precisely the same as that described in Example 14 with the exception that Fragmin® was exchanged for heparin. Eight rabbits received the following doses: Heparin 2 mg/kg, Lipids 100 mg/kg and distilled water 400 mg/kg. All rabbits in this experiment had detectable levels of anti-FXa activity in plasma. The maximal plasma concentration (C $_{max}$) was reached within 0.5–2.0 hours and ranged between 0.12 IU/ml to 0.53 IU/ml. The average absorption in this experiment was 15.7%±8%.

Conclusions: The rectal absorption of heparin is significantly increased when a solution thereof is admixed with the lipid system. The degree of absorption, however, is significantly lower than that of Fragmin®, when they are compared under identical conditions. This indicates that there is a size dependency or specific interaction in the absorption pattern of molecules of heparin origin, which give possibilities to design and control the preparations to be administered.

Example 19

All the samples described so far were injected 10 minutes after preparing the Fragmin®/lipid/water composition.

3 rabbits which received lipid/saline composition containing 4% Fragmin® were checked in order to ascertain whether or not the time lapse between preparing the composition and its administration had any influence on absorption.

The mixture was prepared as in Example 14, but in addition it was allowed to stand for 16 hours before being injected rectally in a dose of Fragmin® 2 mg/kg, lipids 50 mg/kg and physiological saline 200 mg/kg body weight. All rabbits in this experiment had detectable levels of anti-FXa activity in plasma. $C_{max}$ was reached within 0.5–2.0 hours and ranged in between 0.72 IU/ml to 1.90 IU/ml with an average of 1.12 IU/ml. The average absorption in this experiment was about 65%.

Conclusion: The data demonstrates that after being formed, the composition, can be administered after standing for different lengths of time without significant influence on the absorption properties.

Example 20

In vitro experiments were carried out in order to study the influence of the lipid composition on the Fragmin® anti-FXa activity in terms of time of storage. Fragmin® was incorporated into the lipid system as defined in the examples above. The concentration of Fragmin® was 2% by weight of the lipids. One part (weight) of the Fragmin®/lipid and 4 parts(weight) of distilled water were mixed by shaking and then allowed to stand for 6 weeks. The Fragmin® activity was tested regularly over this period. The initial activity 85 IU/mg (series 1)and 78 IU/mg(series 2), respectively, and the activity after 6 weeks was 96 IU/mg (series 1) and 85 IU/mg (series 2).

Conclusion: The results shows that the Fragmin® activity is retained during prolonged storage of the composition.

Example 21

The same procedure as in Example 19 was performed on 4 rabbits with a lipid/saline composition of 2% Fragmin®. The administered dose of Fragmin® was 2 mg/kg with 100 mg/kg lipids and 200 mg/kg of saline. All animals had detectable levels of anti-Fx activity in plasma. $C_{max}$ was reached within 0.75–1.5 h and ranged between 0.82 IU/ml and 0.86 IU/ml, with a mean value of 0.86 IU/ml. The average absorption in this experiment was about 48%.

Conclusion: The dispersion was easy to administrate, and to adjust for the calculated volumes and showed enhanced absorption of Fragmin®.

We claim:
1. A pharmaceutical composition comprising:
   a) a well defined lipid system containing:
      i) at least one amphiphatic, polar and bilayer forming phospholipid component in an amount of 5 to 50 w/w of the lipid system; and ii) a non-polar lipid component comprising a mixture of monoglycerides wherein the fatty acid portion of each of said monoglycerides is from an acid selected from the group consisting of 8:0 caprylic acid and 10:0 capric acid;

b) a therapeutically effective amount of a heparin present in an amount of 1–200% (w/w) with respect to said lipid system; and c) water present in amount such that individual lipid particles are formed spontaneously when interacting with excess water.

2. A composition according to claim 1, characterized in that it is adapted for oral, rectal, buccal, sublingual, nasal, subcutaneous or transdermal use or for administration to mucous membranes and further comprises excipients.

3. A composition according to claim 1 characterized in that said amphiphatic and polar phospholipid components is phosphaditylcholine.

4. A composition according to claim 1 characterized in that said heparin is present in an amount of between 4–80% (w/w) with respect to said lipid system.

5. A composition according to claim 1 characterized in that said heparin is a low molecular weight fragment of heparin with a molecular mass of about 2000–10000 Da.

6. A topical preparation containing the composition according to claim 1 and excipients.

7. A method for preparing the composition according to claim 1 which comprises adding a solution of said heparin to a stirred mixture of said lipid components, thereafter adding the water containing solvent and treating the resultant mixture mechanically, or mixing said heparin with said water containing solvent before adding the mixture to the stirred lipid components.

8. A composition according to claim 2 characterized in that said amphiphatic and polar phospholipid components is phosphaditylcholine.

9. A composition according to claim 2 characterized in that said heparin is present in an amount of between 4–80% (w/w) with respect to said lipid system.

10. A composition according to claim 3 characterized in that said heparin is present in an amount of between 4–80% (w/w) with respect to said lipid system.

11. A composition according to claim 2 characterized in that said heparin is a low molecular weight fragment of heparin with a molecular mass of about 2000–10000 Da.

12. A composition according to claim 3 characterized in that said heparin is a low molecular weight fragment of heparin with a molecular mass of about 2000–10000 Da.

13. A composition according to claim 4 characterized in that said heparin is a low molecular weight fragment of heparin with a molecular mass of about 2000–10000 Da.

14. A method for preparing the composition according to claim 3 which comprises adding a solution of said heparin to a stirred mixture of said lipid components, thereafter adding the water containing solvent and treating the resultant mixture mechanically, or mixing said heparin with said water containing solvent before adding the mixture to the stirred lipid components.

15. A composition according to claim 1, wherein the non polar component further comprises a triglyceride which consists essentially of 8:0 caprylate and 10:0 caprate.

* * * * *

UNITED STATES PATENT AND TRADEMARK OFFICE
CERTIFICATE OF CORRECTION

PATENT NO. : 5,626,869
DATED : May 6, 1997
INVENTOR(S) : Nyqvist, et. al.

It is certified that error appears in the above-indentified patent and that said Letters Patent is hereby corrected as shown below:

Title page, [*] Notice: should read-- The term of this patent shall not extend beyond the expiration date of Pat. No. 5,665,379--.

Signed and Sealed this

Twenty-third Day of September, 1997

Attest:

BRUCE LEHMAN

Attesting Officer

Commissioner of Patents and Trademarks